US008430879B2

(12) United States Patent
Stoneburner et al.

(10) Patent No.: US 8,430,879 B2
(45) Date of Patent: Apr. 30, 2013

(54) SEGMENTED INTRAMEDULLARY STRUCTURE

(75) Inventors: James D. Stoneburner, Santa Clara, CA (US); Matthew T. Harmon, Santa Cruz, CA (US); Roelof Trip, Duluth, GA (US); Charles E. Larsen, Tampa, FL (US); Daniel F. Justin, Logan, UT (US); Karen E. Mohr, Logan, UT (US); Carlyle J. Creger, River Heights, UT (US); Mojan Goshayesh, Atherton, CA (US)

(73) Assignee: Sonoma Orthopedic Products, Inc., Santa Rosa, CA (US)

(*) Notice: Subject to any disclaimer, the term of this patent is extended or adjusted under 35 U.S.C. 154(b) by 1203 days.

(21) Appl. No.: 12/052,919

(22) Filed: Mar. 21, 2008

(65) Prior Publication Data
US 2008/0287951 A1 Nov. 20, 2008

Related U.S. Application Data

(60) Provisional application No. 60/896,342, filed on Mar. 22, 2007.

(51) Int. Cl.
*A61B 17/56* (2006.01)
(52) U.S. Cl.
USPC .............................. 606/74; 606/62; 606/103
(58) Field of Classification Search ................ 606/86 A, 606/103, 74, 321, 62–68; 254/245–247
See application file for complete search history.

(56) References Cited

U.S. PATENT DOCUMENTS

| 2,998,007 | A |   | 8/1961  | Herzog |
|-----------|---|---|---------|--------|
| 3,441,017 | A | * | 4/1969  | Kaessmann ............... 606/64 |
| 3,759,257 | A |   | 9/1973  | Fischer et al. |
| 3,760,802 | A |   | 9/1973  | Fischer et al. |
| 3,846,846 | A |   | 11/1974 | Fischer |
| 4,050,464 | A | * | 9/1977  | Hall ...................... 606/86 A |
| 4,091,806 | A |   | 5/1978  | Aginsky |
| 4,204,531 | A |   | 5/1980  | Aginsky |
| 4,227,518 | A |   | 10/1980 | Aginsky |
| 4,262,665 | A |   | 4/1981  | Roalstad et al. |

(Continued)

FOREIGN PATENT DOCUMENTS

| DE | 2657303 A1   | 6/1977 |
| DE | 10003331 A1  | 8/2001 |

(Continued)

OTHER PUBLICATIONS

PCT Notification of Transmittal of the International Search Report and the Written Opinion of the Searching Authority in PCT/US2008/057868 dated Sep. 22, 2008 in 16 pages.

(Continued)

*Primary Examiner* — Jan Christopher Merene
(74) *Attorney, Agent, or Firm* — Knobbe Martens Olson & Bear LLP

(57) ABSTRACT

An implantable intramedullary fixation structure adapted to be received in the intramedullary canal of a long bone is disclosed comprising a plurality of elongated segments. Each segment has a first end and a complementarily-shaped second end such that the first end of a segment cooperatively engages the second end of an adjacent segment. The segments define a guide aperture so as to be receivable over a guide for positioning in the intramedullary canal.

8 Claims, 14 Drawing Sheets

U.S. PATENT DOCUMENTS

| | | |
|---|---|---|
| 4,457,301 A | 7/1984 | Walker |
| 4,522,200 A | 6/1985 | Stednitz |
| 4,653,487 A | 3/1987 | Maale |
| 4,706,659 A | 11/1987 | Matthews et al. |
| 4,721,103 A | 1/1988 | Freedland |
| 4,756,307 A | 7/1988 | Crowninshield |
| 4,776,330 A | 10/1988 | Chapman et al. |
| 4,805,607 A | 2/1989 | Engelhardt et al. |
| 4,846,162 A | 7/1989 | Moehring |
| 4,854,312 A | 8/1989 | Raftopoulos et al. |
| 4,858,602 A | 8/1989 | Seidel et al. |
| 4,875,475 A | 10/1989 | Comte et al. |
| 4,895,572 A | 1/1990 | Chernoff |
| 4,938,769 A | 7/1990 | Shaw |
| 5,002,543 A | 3/1991 | Bradshaw et al. |
| 5,008,398 A | 4/1991 | Koehler et al. |
| 5,019,108 A | 5/1991 | Bertin et al. |
| 5,035,697 A | 7/1991 | Frigg |
| 5,041,114 A | 8/1991 | Chapman et al. |
| 5,041,115 A | 8/1991 | Frigg et al. |
| 5,053,035 A | 10/1991 | McLaren |
| 5,057,103 A | 10/1991 | Davis |
| 5,074,882 A | 12/1991 | Grammont et al. |
| 5,108,437 A | 4/1992 | Kenna |
| 5,112,333 A | 5/1992 | Fixel |
| 5,122,141 A | 6/1992 | Simpson et al. |
| 5,135,527 A | 8/1992 | Ender |
| 5,190,544 A | 3/1993 | Chapman et al. |
| 5,281,225 A | 1/1994 | Vicenzi |
| 5,364,398 A | 11/1994 | Chapman et al. |
| 5,395,374 A * | 3/1995 | Miller et al. ............... 606/74 |
| 5,415,660 A | 5/1995 | Campbell et al. |
| 5,423,850 A | 6/1995 | Berger |
| 5,429,640 A | 7/1995 | Shuler et al. |
| 5,472,444 A | 12/1995 | Huebner et al. |
| 5,480,400 A | 1/1996 | Berger |
| 5,484,439 A | 1/1996 | Olson et al. |
| 5,489,284 A | 2/1996 | James et al. |
| 5,501,695 A | 3/1996 | Anspach, Jr. et al. |
| 5,507,817 A | 4/1996 | Craig et al. |
| 5,516,335 A | 5/1996 | Kummer et al. |
| 5,549,610 A | 8/1996 | Russell et al. |
| 5,562,667 A | 10/1996 | Shuler et al. |
| 5,569,249 A | 10/1996 | James et al. |
| 5,618,286 A | 4/1997 | Brinker |
| 5,620,445 A | 4/1997 | Brosnahan et al. |
| 5,626,580 A | 5/1997 | Brosnahan |
| 5,649,925 A | 7/1997 | Barbera Alacreu |
| 5,653,709 A | 8/1997 | Frigg |
| 5,658,287 A | 8/1997 | Hofmann et al. |
| 5,658,349 A | 8/1997 | Brooks et al. |
| 5,702,389 A | 12/1997 | Taylor et al. |
| 5,702,486 A | 12/1997 | Craig et al. |
| 5,720,753 A | 2/1998 | Sander et al. |
| 5,725,541 A | 3/1998 | Anspach, III et al. |
| 5,772,662 A | 6/1998 | Chapman et al. |
| 5,772,663 A * | 6/1998 | Whiteside et al. ............... 606/74 |
| 5,776,194 A | 7/1998 | Mikol et al. |
| 5,782,865 A | 7/1998 | Grotz |
| 5,849,004 A | 12/1998 | Bramlet |
| 5,855,579 A | 1/1999 | James et al. |
| 5,879,352 A | 3/1999 | Filoso et al. |
| 5,888,208 A | 3/1999 | Ro |
| 5,899,425 A | 5/1999 | Corey Jr. et al. |
| 5,944,719 A | 8/1999 | Leban |
| 6,010,506 A | 1/2000 | Gosney et al. |
| 6,019,761 A | 2/2000 | Gustilo |
| 6,053,922 A | 4/2000 | Krause et al. |
| 6,068,648 A | 5/2000 | Cole et al. |
| 6,083,244 A | 7/2000 | Lubbers et al. |
| 6,106,528 A | 8/2000 | Durham et al. |
| 6,120,504 A | 9/2000 | Brumback et al. |
| 6,123,708 A | 9/2000 | Kilpela et al. |
| 6,126,663 A | 10/2000 | Hair |
| 6,126,691 A | 10/2000 | Kasra et al. |
| 6,127,597 A | 10/2000 | Beyar et al. |
| 6,129,729 A | 10/2000 | Snyder |
| 6,168,595 B1 | 1/2001 | Durham et al. |
| 6,171,342 B1 | 1/2001 | O'Neil et al. |
| 6,183,474 B1 | 2/2001 | Bramlet et al. |
| 6,221,074 B1 | 4/2001 | Cole et al. |
| 6,224,600 B1 | 5/2001 | Protogirou |
| 6,228,086 B1 | 5/2001 | Wahl et al. |
| 6,241,734 B1 | 6/2001 | Scribner et al. |
| 6,248,110 B1 | 6/2001 | Reiley et al. |
| 6,261,289 B1 | 7/2001 | Levy |
| 6,264,699 B1 | 7/2001 | Noiles et al. |
| 6,294,187 B1 | 9/2001 | Boyce et al. |
| 6,296,644 B1 | 10/2001 | Saurat et al. |
| 6,319,286 B1 | 11/2001 | Fernandez et al. |
| 6,322,564 B1 | 11/2001 | Surma |
| 6,322,591 B1 | 11/2001 | Ahrens |
| 6,355,044 B1 | 3/2002 | Hair |
| 6,368,326 B1 * | 4/2002 | Dakin et al. ............... 606/103 |
| 6,371,989 B1 | 4/2002 | Chauvin et al. |
| 6,402,753 B1 | 6/2002 | Cole et al. |
| 6,423,067 B1 | 7/2002 | Eisermann |
| 6,440,444 B2 | 8/2002 | Boyce et al. |
| 6,447,518 B1 | 9/2002 | Krause et al. |
| 6,517,541 B1 | 2/2003 | Sesic |
| 6,524,313 B1 | 2/2003 | Fassier et al. |
| 6,527,775 B1 | 3/2003 | Warburton |
| 6,547,791 B1 | 4/2003 | Buhren et al. |
| 6,551,321 B1 | 4/2003 | Burkinshaw et al. |
| 6,554,833 B2 | 4/2003 | Levy et al. |
| 6,569,165 B2 | 5/2003 | Wahl et al. |
| 6,575,973 B1 | 6/2003 | Shekalim |
| 6,582,453 B1 | 6/2003 | Tran et al. |
| 6,607,531 B2 | 8/2003 | Frigg |
| 6,629,999 B1 | 10/2003 | Serafin, Jr. |
| 6,635,061 B1 | 10/2003 | Snyder |
| 6,660,039 B1 | 12/2003 | Evans et al. |
| 6,663,670 B2 | 12/2003 | Rogers et al. |
| 6,669,701 B2 | 12/2003 | Steiner et al. |
| 6,692,530 B2 | 2/2004 | Doubler et al. |
| 6,696,073 B2 | 2/2004 | Boyce et al. |
| 6,712,855 B2 | 3/2004 | Martin et al. |
| 6,719,759 B2 | 4/2004 | Wagner et al. |
| 6,730,090 B2 | 5/2004 | Orbay et al. |
| 6,736,818 B2 | 5/2004 | Perren et al. |
| 6,740,120 B1 | 5/2004 | Grimes |
| 6,746,407 B2 | 6/2004 | Steuer et al. |
| 6,746,487 B2 | 6/2004 | Scifert et al. |
| 6,755,780 B2 | 6/2004 | Borst et al. |
| 6,755,862 B2 | 6/2004 | Keynan |
| 6,761,722 B2 | 7/2004 | Cole et al. |
| 6,783,530 B1 | 8/2004 | Levy |
| 6,783,551 B1 | 8/2004 | Metzger et al. |
| 6,793,659 B2 | 9/2004 | Putnam |
| 6,887,278 B2 | 5/2005 | Lewallen |
| 6,902,583 B2 | 6/2005 | Gerbec et al. |
| 6,908,465 B2 | 6/2005 | von Hoffmann et al. |
| 6,911,048 B2 | 6/2005 | Fernandez et al. |
| 6,921,400 B2 | 7/2005 | Sohngen |
| 6,926,719 B2 | 8/2005 | Sohngen et al. |
| 6,932,819 B2 | 8/2005 | Wahl et al. |
| 6,953,479 B2 | 10/2005 | Carson et al. |
| 6,960,163 B2 | 11/2005 | Ewers et al. |
| 6,994,725 B1 | 2/2006 | Goble |
| 7,001,386 B2 | 2/2006 | Sohngen et al. |
| 7,008,425 B2 | 3/2006 | Phillips |
| 7,052,498 B2 | 5/2006 | Levy et al. |
| 7,135,022 B2 | 7/2006 | Kosashvili et al. |
| 7,125,423 B2 | 10/2006 | Hazebrouck |
| 7,172,595 B1 | 2/2007 | Goble |
| 7,186,264 B2 | 3/2007 | Liddicoat et al. |
| 7,189,201 B2 | 3/2007 | Borst et al. |
| 7,237,556 B2 | 7/2007 | Smothers et al. |
| 7,250,028 B2 | 7/2007 | Julian et al. |
| 7,258,692 B2 | 8/2007 | Thelen et al. |
| 7,261,713 B2 | 8/2007 | Langmaid et al. |
| 7,267,678 B2 | 9/2007 | Medoff |
| 7,410,483 B2 | 8/2008 | Danitz et al. |
| 7,846,162 B2 | 12/2010 | Nelson et al. |
| 7,909,825 B2 | 3/2011 | Saravia et al. |
| 7,914,533 B2 | 3/2011 | Nelson et al. |
| 7,942,875 B2 | 5/2011 | Nelson et al. |

| | | | | | |
|---|---|---|---|---|---|
| 7,942,876 B2 * | 5/2011 | Hack .................... 606/64 | 2009/0216232 A1 | 8/2009 | Buford et al. |
| 8,128,627 B2 | 3/2012 | Justin et al. | 2009/0228007 A1 | 9/2009 | Justin et al. |
| 2001/0012939 A1 | 8/2001 | Wahl et al. | 2009/0228008 A1 | 9/2009 | Justin et al. |
| 2001/0018616 A1 | 8/2001 | Schwab | 2010/0023010 A1 | 1/2010 | Nelson et al. |
| 2002/0032444 A1 | 3/2002 | Mische | 2010/0094347 A1 | 4/2010 | Nelson et al. |
| 2002/0068939 A1 | 6/2002 | Levy et al. | 2011/0087227 A1 | 4/2011 | Mazur et al. |
| 2002/0099385 A1 | 7/2002 | Ralph et al. | 2011/0144645 A1 | 6/2011 | Saravia et al. |
| 2002/0111629 A1 | 8/2002 | Phillips | 2011/0282346 A1 | 11/2011 | Pham et al. |
| 2002/0133156 A1 | 9/2002 | Cole | | | |
| 2002/0143337 A1 | 10/2002 | Orbay et al. | FOREIGN PATENT DOCUMENTS | | |
| 2002/0151898 A1 | 10/2002 | Sohngen et al. | | | |
| 2002/0188297 A1 * | 12/2002 | Dakin et al. ........... 606/72 | EP | 295041 | 9/1993 |
| 2003/0014120 A1 | 1/2003 | Carson et al. | EP | 0882431 | 10/2002 |
| 2003/0018336 A1 | 1/2003 | Vandewalle | EP | 1278485 | 1/2003 |
| 2003/0050704 A1 | 3/2003 | Keynan | EP | 1522268 | 4/2005 |
| 2003/0069580 A1 | 4/2003 | Langmaid et al. | EP | 1582159 | 10/2005 |
| 2003/0069581 A1 | 4/2003 | Stinson et al. | EP | 1582160 | 10/2005 |
| 2003/0100906 A1 | 5/2003 | Rosa et al. | EP | 1582161 | 10/2005 |
| 2003/0100907 A1 | 5/2003 | Rosa et al. | EP | 1582162 | 10/2005 |
| 2003/0109932 A1 | 6/2003 | Keynan | EP | 1582163 | 10/2005 |
| 2003/0114855 A1 | 6/2003 | Wahl et al. | EP | 1582164 | 10/2005 |
| 2003/0130660 A1 | 7/2003 | Levy et al. | EP | 1815813 | 8/2007 |
| 2003/0139818 A1 | 7/2003 | Rogers et al. | EP | 1820462 | 8/2007 |
| 2003/0181918 A1 | 9/2003 | Smothers et al. | FR | 2 801 189 A1 | 11/1999 |
| 2003/0187449 A1 | 10/2003 | Mccleary et al. | WO | WO9222268 | 12/1992 |
| 2003/0195515 A1 | 10/2003 | Sohngen | WO | WO9313713 | 7/1993 |
| 2003/0204269 A1 | 10/2003 | Gerbec et al. | WO | WO9512358 | 4/1997 |
| 2004/0087955 A1 | 5/2004 | Bordi | WO | WO9718769 | 5/1997 |
| 2004/0133204 A1 | 7/2004 | Davies | WO | WO 97/39693 | 10/1997 |
| 2004/0153082 A1 | 8/2004 | Howie et al. | WO | WO9818397 | 5/1998 |
| 2004/0193267 A1 | 9/2004 | Jones et al. | WO | WO9836699 | 8/1998 |
| 2004/0193268 A1 | 9/2004 | Hazebrouck | WO | WO 98/38918 | 9/1998 |
| 2004/0230193 A1 | 11/2004 | Cheung et al. | WO | WO 00/19924 | 4/2000 |
| 2005/0010223 A1 | 1/2005 | Gotfried | WO | WO0044319 | 8/2000 |
| 2005/0033366 A1 | 2/2005 | Cole et al. | WO | WO0044321 | 8/2000 |
| 2005/0055023 A1 | 3/2005 | Sohngen et al. | WO | WO0044946 | 8/2000 |
| 2005/0070902 A1 | 3/2005 | Medoff | WO | WO0149193 | 7/2001 |
| 2005/0071014 A1 | 3/2005 | Barnett et al. | WO | WO02071961 | 9/2002 |
| 2005/0075635 A1 | 4/2005 | Semet | WO | WO03068090 | 8/2003 |
| 2005/0075637 A1 | 4/2005 | Semet | WO | WO2005094705 | 10/2005 |
| 2005/0107793 A1 | 5/2005 | Manderson | WO | WO2005094706 | 10/2005 |
| 2005/0125067 A1 | 6/2005 | Sweeney | WO | WO2005096976 | 10/2005 |
| 2005/0187550 A1 | 8/2005 | Grusin | WO | WO2005102196 | 11/2005 |
| 2005/0216007 A1 | 9/2005 | Woll et al. | WO | WO 2005/112804 | 12/2005 |
| 2005/0271694 A1 | 12/2005 | Mansouri et al. | WO | WO2006041460 | 4/2006 |
| 2005/0273103 A1 | 12/2005 | Wahl et al. | WO | WO 2007/019123 | 1/2007 |
| 2005/0277936 A1 | 12/2005 | Siravo et al. | WO | WO2007008177 | 1/2007 |
| 2006/0004459 A1 | 1/2006 | Hazebrouck et al. | WO | WO2007053960 | 5/2007 |
| 2006/0004465 A1 | 1/2006 | Bergin et al. | WO | WO2008116170 | 9/2008 |
| 2006/0009774 A1 | 1/2006 | Goble et al. | WO | WO2008116175 | 9/2008 |
| 2006/0009853 A1 | 1/2006 | Justin et al. | | | |
| 2006/0009854 A1 | 1/2006 | Justin et al. | OTHER PUBLICATIONS | | |
| 2006/0009855 A1 | 1/2006 | Goble et al. | | | |
| 2006/0030945 A1 | 2/2006 | Wright | | | |
| 2006/0041317 A1 | 2/2006 | Hazebrouck et al. | | | |
| 2006/0167464 A1 * | 7/2006 | Allen et al. ............ 606/103 | | | |
| 2006/0264950 A1 | 11/2006 | Nelson et al. | | | |
| 2006/0264951 A1 | 11/2006 | Nelson et al. | | | |
| 2006/0264952 A1 | 11/2006 | Nelson et al. | | | |
| 2007/0016194 A1 | 1/2007 | Shaolian et al. | | | |
| 2007/0123877 A1 | 5/2007 | Goldin et al. | | | |
| 2007/0169782 A1 | 7/2007 | Smothers et al. | | | |
| 2007/0173834 A1 | 7/2007 | Thakkar | | | |
| 2007/0208223 A1 | 9/2007 | Julian et al. | | | |
| 2007/0250113 A1 | 10/2007 | Hegeman et al. | | | |
| 2008/0065116 A1 | 3/2008 | Lee et al. | | | |
| 2008/0132896 A1 | 6/2008 | Bowen et al. | | | |
| 2008/0140078 A1 | 6/2008 | Nelson et al. | | | |
| 2008/0161805 A1 | 7/2008 | Saravia et al. | | | |
| 2008/0255560 A1 | 10/2008 | Myers et al. | | | |
| 2009/0018542 A1 | 1/2009 | Saravia et al. | | | |

PCT Invitation to Pay Additional Fees with Search Results in PCT/US2009/044898 dated Aug. 27, 2009 in 6 pages.
PCT Notification of Transmittal of the International Search Report and the Written Opinion of the Searching Authority in PCT/US2009/044898 dated Dec. 7, 2010 in 16 pages.
Darron M. Jones et al., "Focal Osteolysis at the Junctions of a Modular Stainless-Steel Femoral Intramedullary Nail", The Journal of Bone & Joint Surgery • jbjs.org vol. 83-A • No. 4 • Apr. 2001, pp. 537-548.
"The Titanium Flexible Humeral Nail System: Quick Reference for Surgical Technique" Synthes publication from Jul. 1999.
PCT International Search Report in PCT /US2008/057868 dated Jul. 8, 2008.
PCT International Search Report and Written Opinion in PCT /US2008/057868 mailed Sep. 22, 2008.
European Communication pursuant to Article 94(3) EPC in European App. No. 09751602.5, dated Jul. 1, 2011 in 4 pages.

* cited by examiner

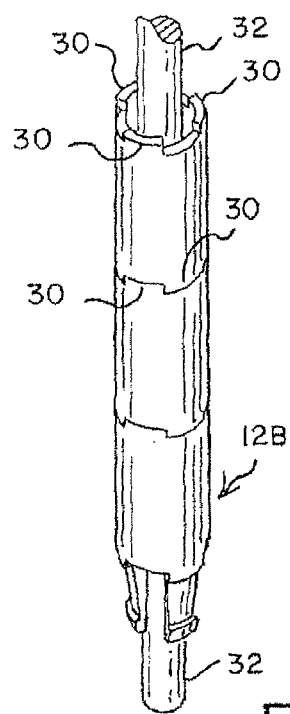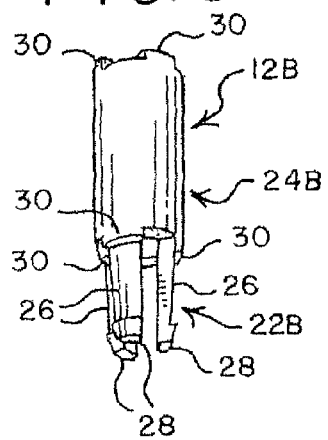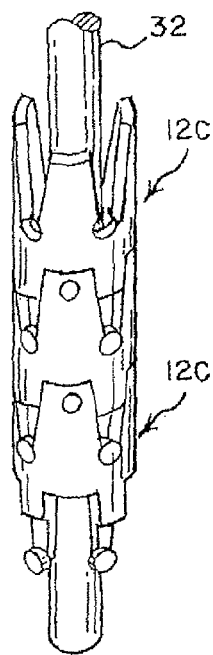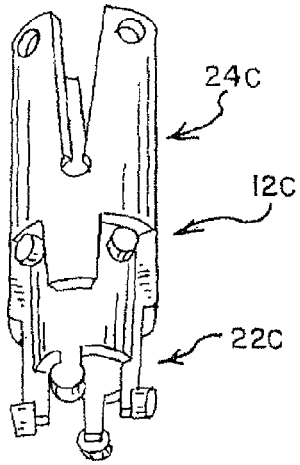

FIG. 9
FIG. 10
FIG. 11
FIG. 12
FIG. 13
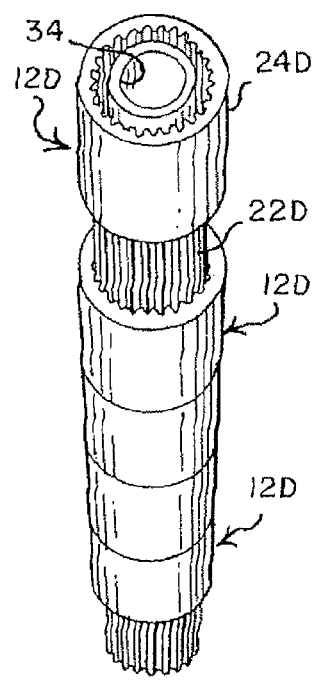
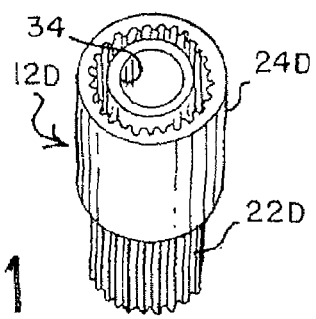
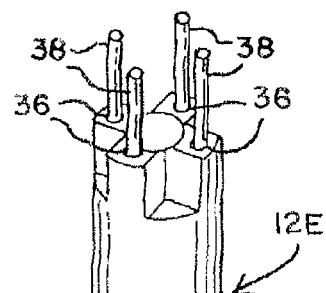
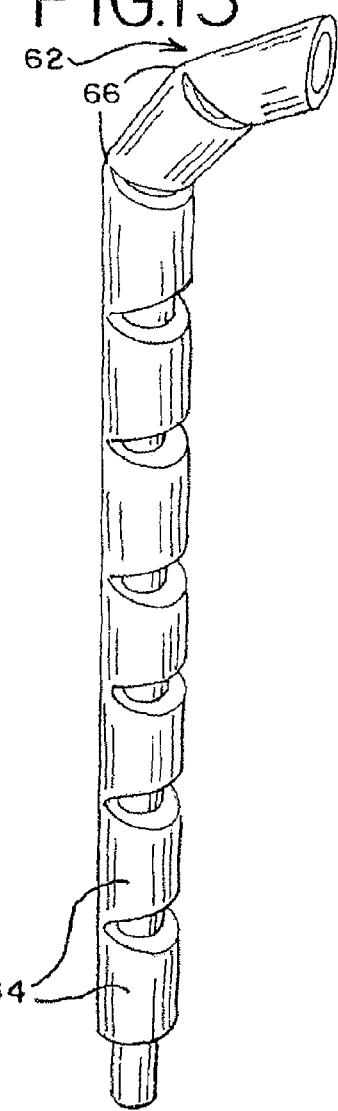
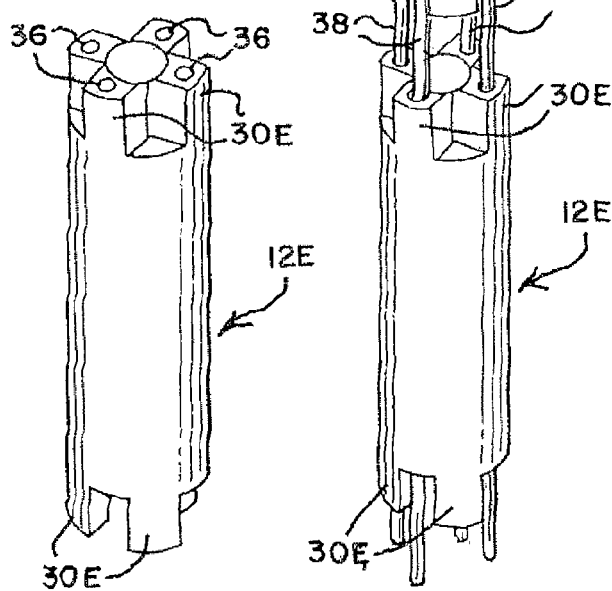

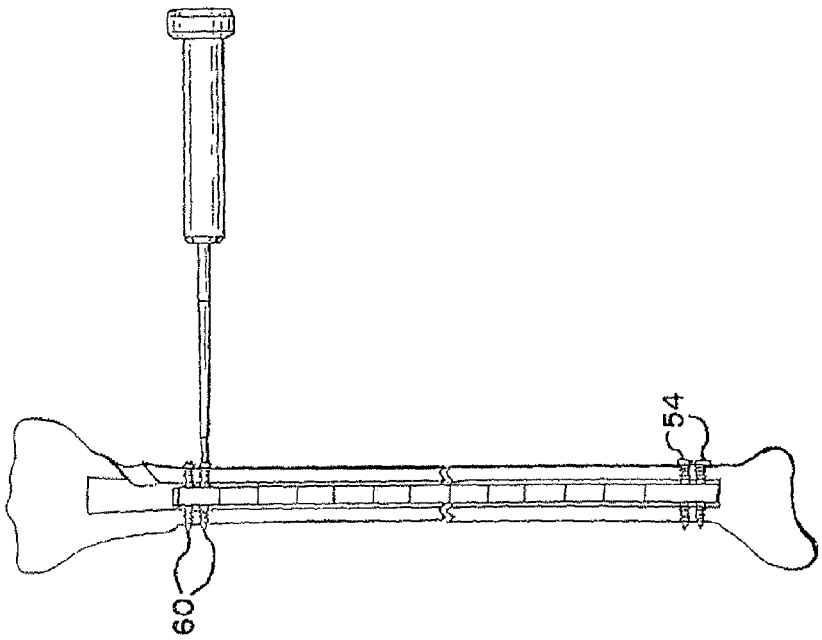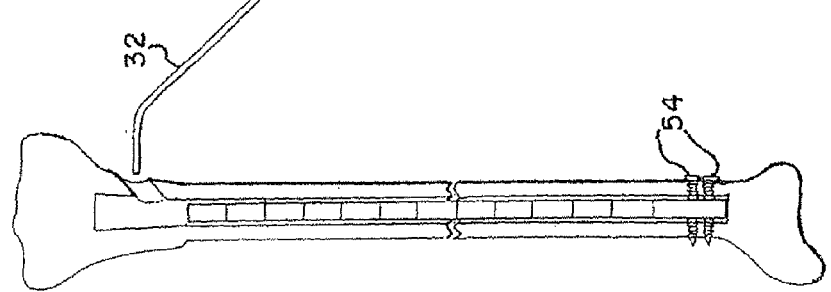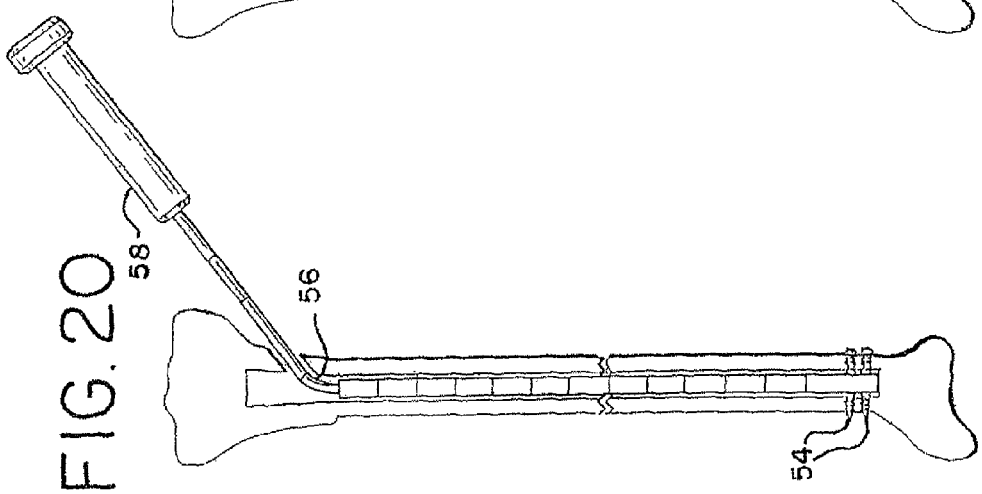

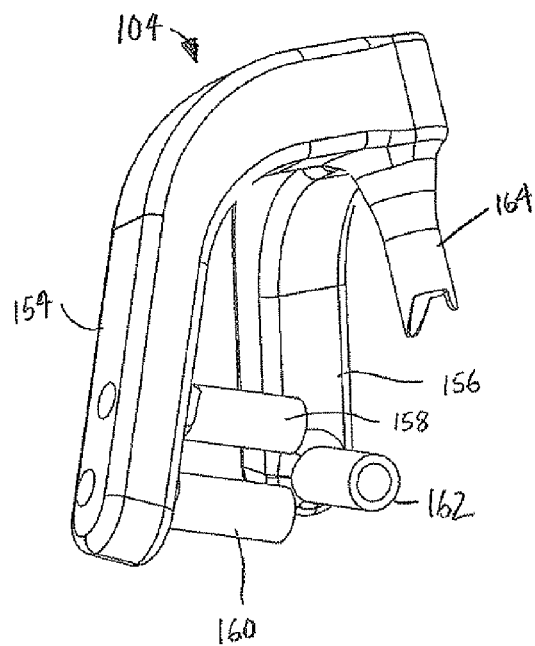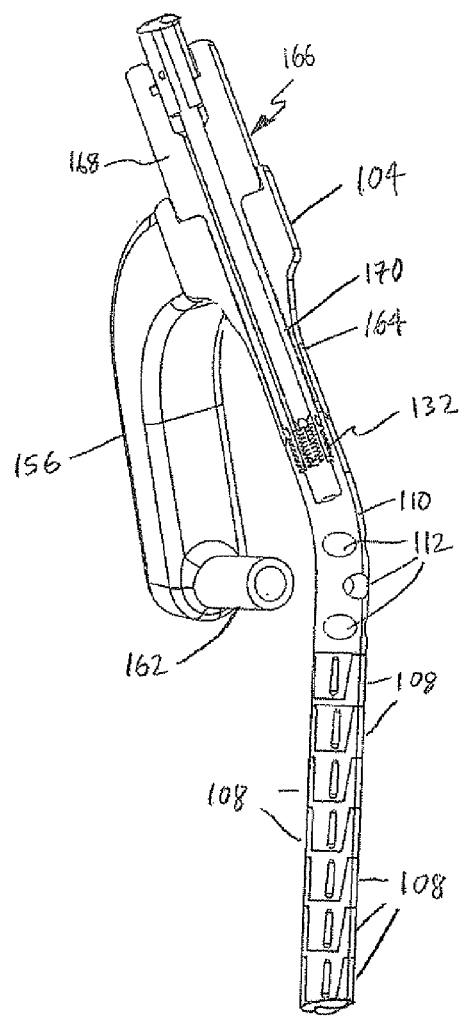

US 8,430,879 B2

SEGMENTED INTRAMEDULLARY STRUCTURE

CROSS REFERENCE TO RELATED APPLICATION

This application claims the benefit of the filing date of U.S. Provisional Application Ser. No. 60/896,342, filed Mar. 22, 2007, the entire contents of which are incorporated by reference herein.

BACKGROUND

The present invention relates an orthopedic prosthesis, and, more particularly, to an implantable structure, commonly called an intramedullary or IM nail, that is adapted to be received in the intramedullary canal for the treatment of long bone fractures.

SUMMARY

The intramedullary structure of the present disclosure, in one embodiment, utilizes a plurality of segments that are preferably introduced into the intramedullary canal over a guide member that has been previously introduced into the intramedullary canal through a percutaneous access hole. Each segment is preferably configured so that it interconnects with the segments adjacent thereto. Also preferably, an elongated tensioning member is received interiorly of the segments and is secured to the end segments to secure all the segments in the structure together. In one embodiment, the guide member is a wire or cable that also serves as the tensioning member.

More specifically, each segment may have an aperture, in the form of an open interior, so that the segment can be threaded over a guide or tensioning member. The segments also have opposed ends that preferably are complementarily-shaped so that an end of a first segment is adapted to cooperatively engage with the end of a second segment adjacent thereto. Preferably, each segment has a male end and a complementarily-shaped female end.

Other features and aspects will become apparent upon reference to the accompanying drawings and description.

BRIEF DESCRIPTION OF THE DRAWINGS

FIGS. 5 and 6 are perspective views of a third embodiment of an individual segment for use in an intramedullary structure and a plurality of such segments received over a guide member.

FIGS. 7 and 8 are perspective views of a fourth embodiment of an individual segment and a plurality of such structures received over a guide member.

FIGS. 9 and 10 are perspective views of a fifth embodiment of an individual segment and a plurality of such segments mounted together.

FIGS. 11 and 12 are perspective views of a sixth embodiment of a segment for use in an intramedullary nail in which a plurality of peripheral rods is used in the assembled nail.

FIG. 13 is a perspective of a seventh embodiment of an IM nail in which the segments are connected to each other by a hinge member so that the nail can be inserted into the intramedullary canal through an access hole that is oblique to the axis of the intramedullary canal.

FIGS. 14-22 schematically illustrate the procedure for installing a segmented intramedullary nail according to the present disclosure into the intramedullary canal of a long bone.

FIG. 34 is a perspective view of a screw guide interface adapted to be seated on the proximal end of the implantable fracture fixation device shown in FIG. 23.

FIG. 35 is a cross-sectional view of the screw guide interface and the proximal end of the fracture fixation structure shown in FIG. 24.

DETAILED DESCRIPTION

In accordance with the present disclosure, an intramedullary structure is provided that is adapted to be received in the intramedullary canal of a long bone, such as a tibia. The structure comprises a plurality of elongated segments, with each segment having a first end and a complementarily-shaped second end, so that the first end of a segment cooperatively engages the second end of an adjacent segment. The segments preferably define a guide wire aperture so as to be receivable over a guide wire or cable for introduction into the intramedullary canal. Optionally, the structure may include a tensioning member in the form of, e.g., a cable or a rod extending the length thereof that cooperates with the end-most segments of the structure to apply a compressive force along the longitudinal axis of the structure, thus providing the structure with enhanced rigidity.

Figure 1:
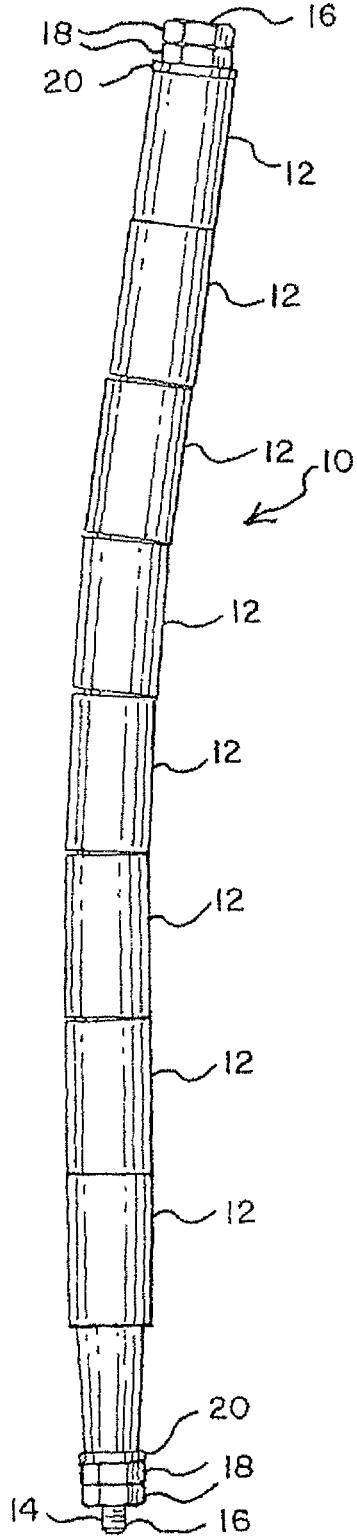
FIG. 1 is a perspective of an assembled segmented intramedullary structure, such as a nail, according to a first embodiment of the disclosure.

Turning to FIG. 1, a first embodiment of a segmented intramedullary structure 10 is shown. The illustrated structure comprises eight segments 12 that are received over an optional tension rod 14 to provide an intramedullary structure 10 having an overall length of approximately 175 mm. Of course, the number of segments 12 and the overall length of the nail will depend upon the length of the intramedullary canal into which it is to be inserted.

As shown, the ends 16 of the tension rod 14 are threaded and the segments 12 are maintained thereon by complementarily threaded members (nuts 18 and washers 20 are shown) received on the threaded ends 16 of the tension rod 14. However, alternate methods for securing the segments 12 to the tension rod 14 may be employed, such as a swage fitting that is received on the tension rod and which seats in the open interior of the end segments, or a press nut received on the tension rod in engagement with the end segments.

Figure 2:
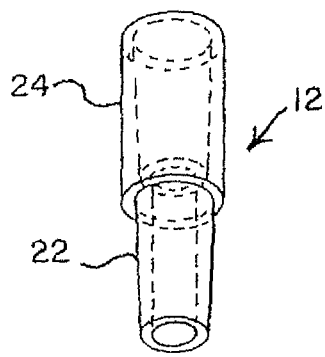
FIG. 2 is a perspective view of a single segment of the intramedullary nail of FIG. 1
Figure 3:
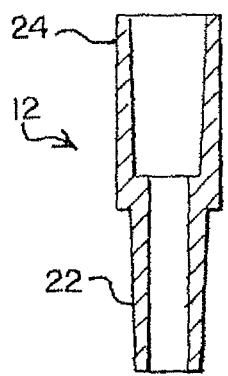
FIG. 3 is a longitudinal cross-sectional view of the segment of FIG. 2.

FIGS. 2 and 3 show a single segment 12 of the intramedullary structure shown in FIG. 1. The specific configuration of the individual segment 12 shown in FIGS. 2 and 3 is by way of example only. The segment 12 comprises a male end 22 having a frusto-conical outer shape and a female end 24 having a cylindrical outer shape and a frusto-conical inner shape complementarily to the outer shape of the male end 22.

The overall length of the segment 12 is preferably no greater than about 32 mm, which allows the segment 12 to be relatively easily introduced into the intramedullary canal through a 10 mm percutaneous access hole that is oriented at approximately 30 degrees with respect to the bone axis. The largest outside diameter of the segment 12 is dictated by the inside diameter of the intramedullary canal, and is typically about 9 mm. The inside diameter of the male end 22 of the segment is approximately 3.6 mm, which allows a 3 mm guide wire or cable to easily pass therethrough.

The segments 12 are made of a biocompatible material of sufficient rigidity and strength, such as titanium. The inside surface of the female end 24 and the outside surface of the male end 22 may be smooth ("mirror polished") to facilitate nesting. The outside surface of the female end 24 may be roughened or textured ("knurled") to promote tissue growth thereon.

In the illustrated embodiment, adjacent segments 12 are secured to each other by a friction fit between the inside surface of the female end and the outside surface of the male end. However, a more positive interlocking can be obtained, if desired, by providing the segments with mechanically-interlocking structures, such as slots and pins, prongs, tabs, screw threads, etc. The segments may also be configured to prevent rotational movement therebetween when assembled. This may be accomplished by, e.g., providing the outer surface of the male end and the inner surface of the female end with complementary non-circular cross sections, such as a square with rounded-off corners. Alternatively, or additionally, a bone cement or other hardenable surgical fluid may be introduced into the interior of the segments once in place in the intramedullary canal, to impart additional structural integrity for the assembly and to help secure the assembled structure in place.

Figure 4:
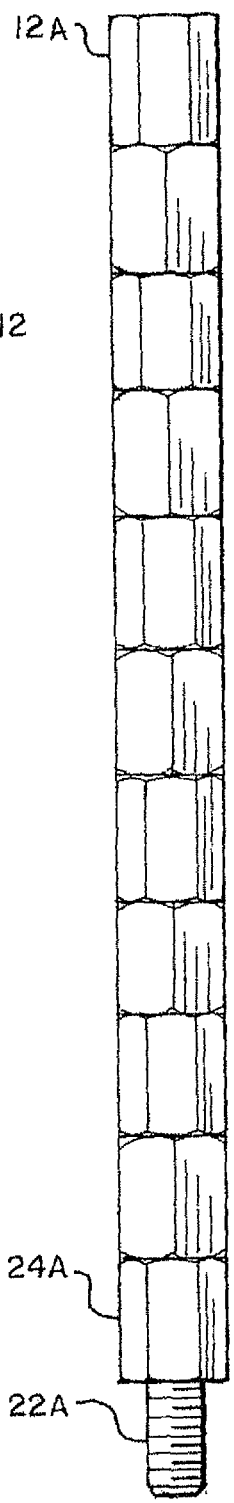
FIG. 4 is a perspective view of an intramedullary nail utilizing a second embodiment of an individual nail segment.

FIG. 4 illustrates an IM structure in accordance with the present disclosure utilizing a second embodiment of individual segments 12A. The male end 22A of the segments 12A comprise an externally-threaded standoff that is received in the complementary internally threaded female end 24A of an adjacent segment 12A.

FIGS. 5 and 6 disclose a third embodiment of segments 12B for an IM structure in accordance with the present disclosure. The male ends 22B of the segments comprise prongs 26 with shoulders or detents 28 on their distal ends that provide for a snap fit with the complementarily-shaped end 24B of the adjacent segment 12B. A series of interfitting spaced tabs 30 on the periphery of both the male and female ends provides for alignment of the segments and serve to prevent rotation of the segments 12B with respect to each other. When introduced into the intramedullary canal, the segments are preferably received over a rod or guidewire 32 to facilitate their mating engagement.

FIGS. 7 and 8 disclose a fourth embodiment of segments 12C for use in an IM structure that is similar to the embodiments of FIGS. 4 and 5. However, the segments 12C have a more elaborate interlocking configuration of the tabs, prongs and detents.

FIGS. 9 and 10 illustrate a fifth embodiment of segments 12D for an IM structure in accordance with the present disclosure. The male end 22D of the segment presents a plurality of longitudinal splines that provide a cross-section similar in appearance to a gear. The female end 24D has a complementarily gear shape and includes a concentric ring 34 that provides a close fit with the inside diameter of the male end 22D. As can be appreciated, this configuration also provides for interfitting segments that are not rotatable with respect to each other.

FIGS. 11 and 12 illustrate a sixth embodiment of segments 12E for use in an IM structure according to the present disclosure. The segments 12E are generally cylindrical in configuration with complementary interfitting tabs 30E on their male and female ends 22E, 24E. The segments 12E also contain a number of spaced, longitudinal throughbores 36 in the walls of the segments (four such throughbores 36 shown. The throughbores 36 receive elongated peripheral rods 38 that provide the assembled IM structure with additional rigidity and strength.

With reference to FIG. 13, a further embodiment of an IM structure 62 is shown. The structure 62 comprises a plurality of segments 64 that are joined to each other by a hinge member 66. The hinge 66 permits the segments to pivot with respect to each other to facilitate introduction of the structure into the intramedullary nail through an angled access hole. As shown, the IM structure is made of a single cylindrical member with the V-shaped notches cut out at regular intervals along the length of the structure, the material from which the cylindrical member is made providing a "living hinge" between the adjacent segments at the apex of each notch. Once inserted into the intramedullary canal, a bone cement is introduced to keep the IM structure straight and provide further structural integrity.

FIGS. 14-22 schematically illustrate the insertion of a segmented intramedullary structure according to the present invention into the intramedullary canal 40 of a long bone 42, such as a tibia.

Figure 14:
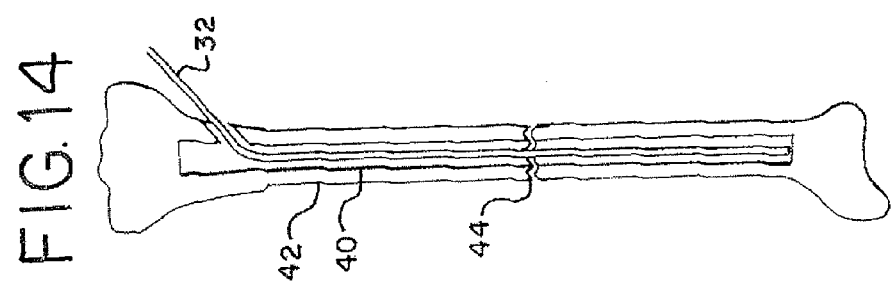

With reference to FIG. 14, a long bone 42 is shown having a fracture 44 intermediate its proximal and distal ends. An access hole 46 is percutaneously made into the intramedullary canal 40 at the proximal end of the intramedullary canal 40 at an angle oblique to the axis or centerline of the long bone, and preferably at an angle of approximately 30 degrees with respect to the axis of the long bone. The access hole 46 is of a diameter to accommodate the introduction of the individual segments 12 that comprise the intramedullary structure. In the present invention, the access hole 46 is approximately 10 mm in diameter. After the access hole 46 is made, a guide wire or cable 32 is inserted therethrough and advanced into the intramedullary canal 40 and across the fracture site 44 to the distal end of the intramedullary canal 40.

Figure 16:
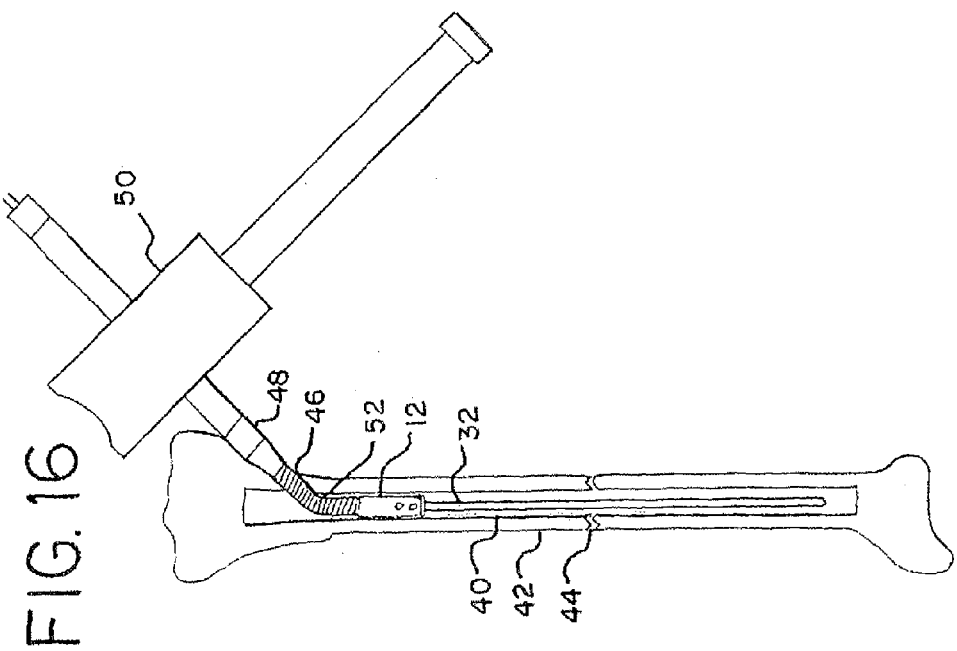
Figure 15:
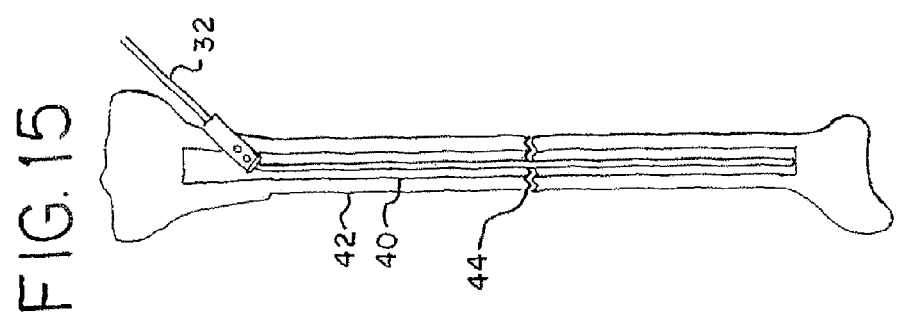

Turning to FIG. 15, the second step is shown in which a first or distal-most segment 12 is threaded over the guidewire and advanced through the percutaneous access hole 46 into the intramedullary canal 40. As shown in FIG. 16, the segment 12 is forced through the access hole 46 and advanced along the guidewire 32 by means of an inserter 48 that also fits over the guidewire 32. The inserter 48 has a slotted hammer 50 associated therewith to impart additional force to the segment 12 as it is advanced into the intramedullary canal 40.

Figure 18:
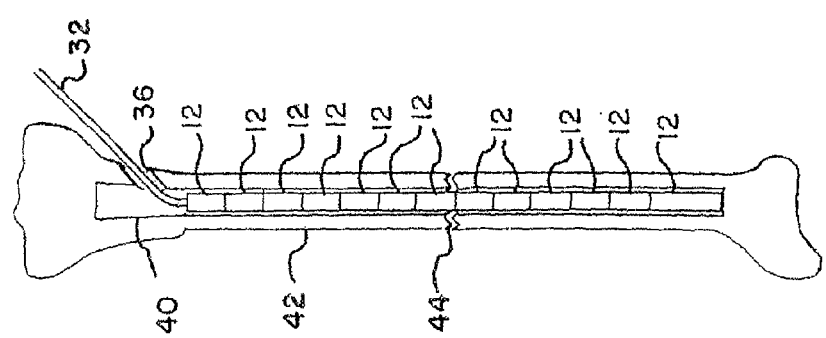
Figure 17:
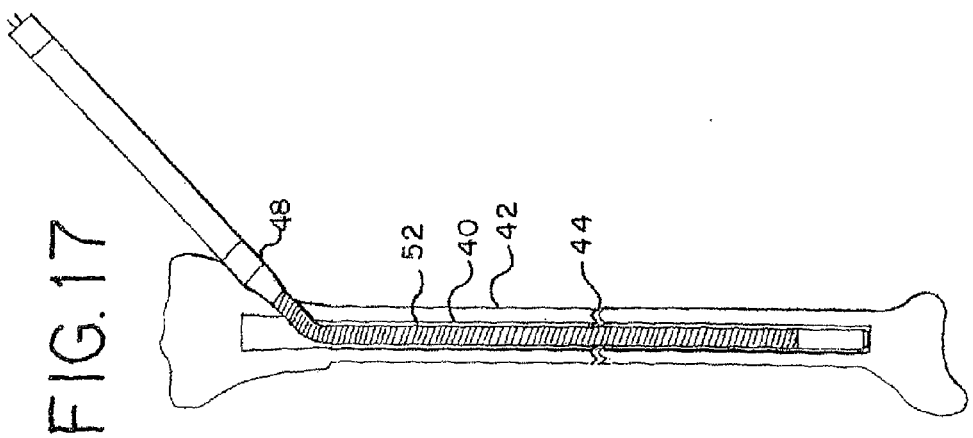
Figure 23:
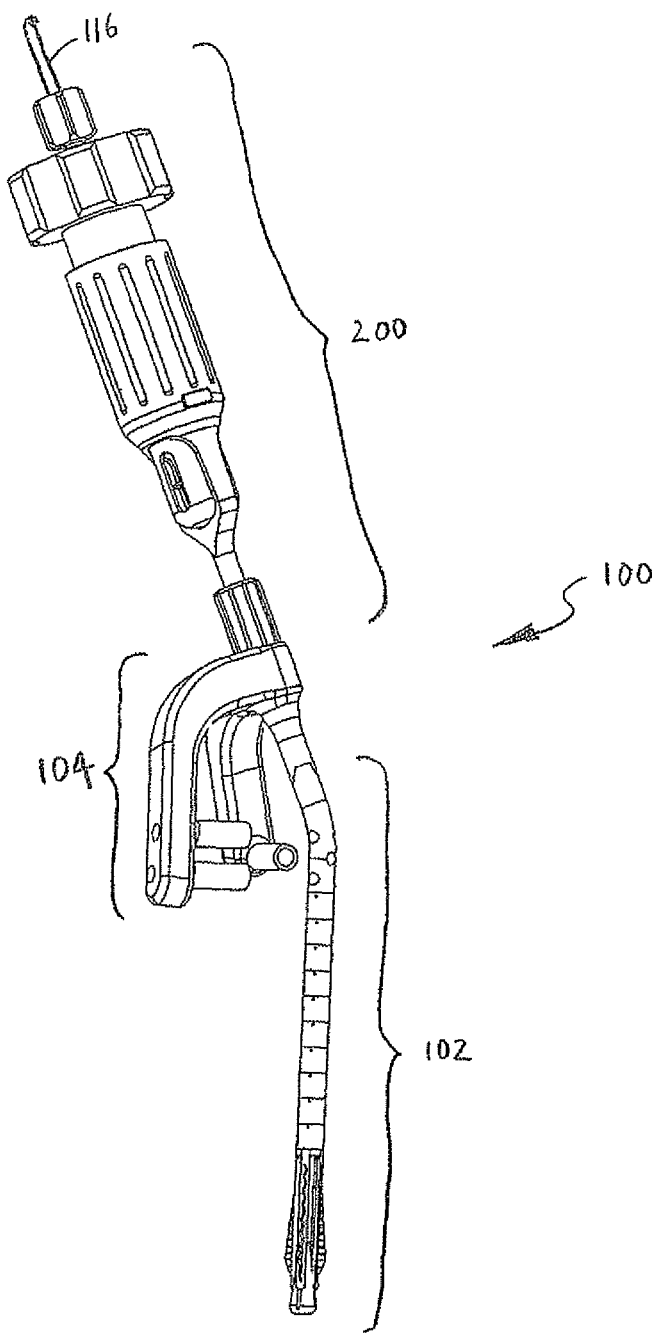
FIG. 23 is a perspective view of a system for implanting an intramedullary fracture fixation device comprising the implantable fracture fixation device, a screw guide, and a cable tensioner.

With reference to FIG. 17, once the segment 12 is positioned within the intramedullary canal 40, it is advanced along the guidewire 32 to the distal end of the IM canal 40 using a flexible push rod 52. The steps of inserting a segment 12 over the guidewire and advancing it distally along the guidewire, shown in FIGS. 15-17, are repeated until an IM structure of the desired length is created. With reference to FIG. 18, the IM structure has thirteen segments. Therefore the steps of FIGS. 15-17 are repeated twelve times.

Figure 19:
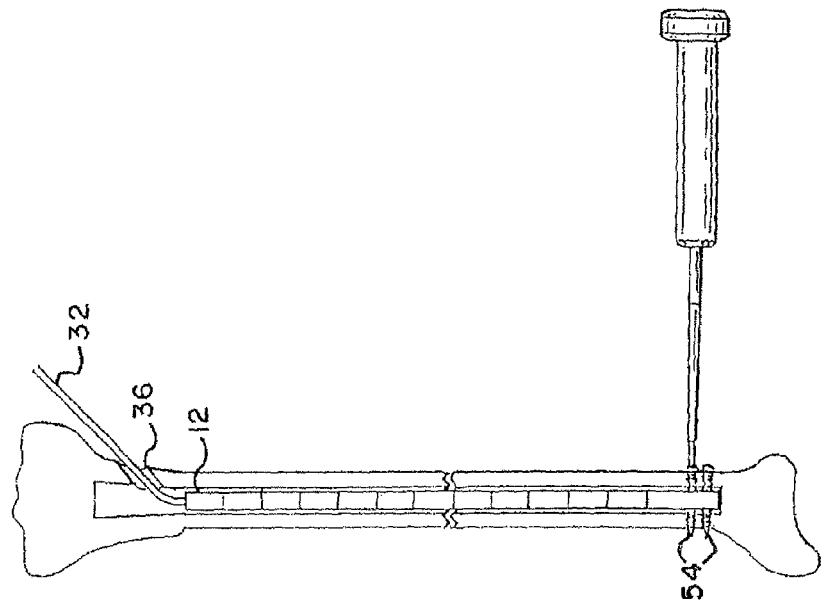

With reference to FIG. 19, the IM structure is secured to the distal end of the IM canal. To this end, the distal-most and proximal-most segments include throughbores for receiving bone screws. Locking bolts 54 are introduced percutaneously and are advanced through bores in the distal-most and proximal-most segments, using fluoroscopy for guidance. In the illustrated method, the guidewire 32 is left in place. However, if the segments comprising the IM nail positively interlock, the guidewire 32 may be removed after all the segments comprising the IM nail are interconnected. With reference to FIG. 20, a locking nut 56 is inserted over the guidewire 32 and into the proximal-most segment, a flexible driver 58 being used to tighten the nut 56 to a prescribed torque. The exposed portion of the guidewire 32 is then cut off (FIG. 21) and percutaneous locking bolts 60 are used to secure the proximal-most segment in place (FIG. 22). Means other than locking bolts, fixation screws, or other fasteners may be used to secure the IM structure in place in the intramedullary canal, such as a bone cement or other hardenable surgical fluid, or radially expandable elements.

With reference to FIGS. 23-39, a further embodiment of a segmented intramedullary system, generally designated 100, is disclosed. The system 100 comprises three basic components: an implantable segmented intramedullary fracture fixation device structure 102, a proximal fixation screw guide-interface 104, and a cable tensioner assembly 200.

Figure 25:
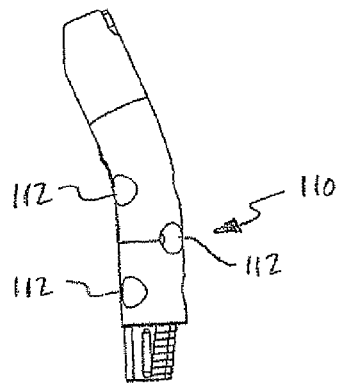
FIG. 25 is a front view of the proximal-most segment of the implantable fracture fixation device shown in FIG. 24.
Figure 24:
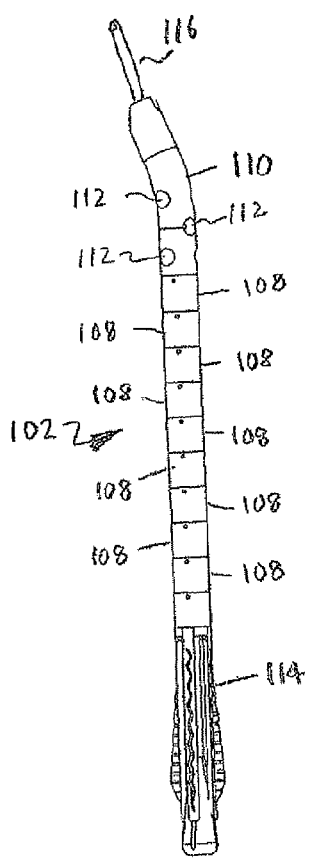
FIG. 24 is a front view of the implantable intramedullary fracture fixation device shown in FIG. 23.
Figure 26:
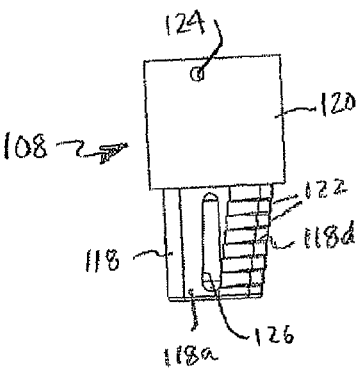
FIG. 26 is a front view of a typical intermediate segment of the implantable fracture fixation device shown in FIG. 24.
Figure 27:
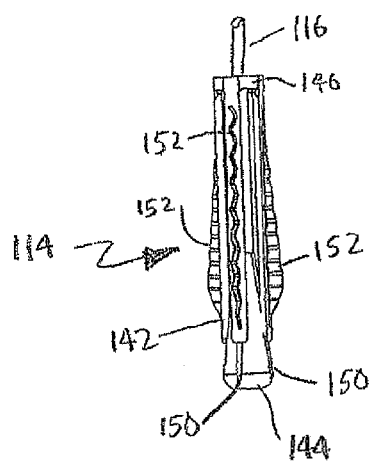
FIG. 27 is a front view of the distal-most segment of the implantable fracture fixation device shown in FIG. 24.
Figure 28:
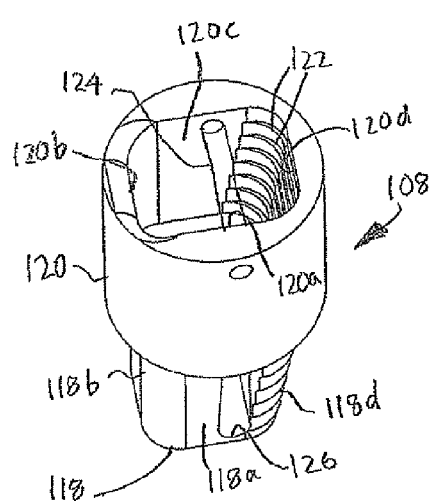
FIGS. 28 and 29 are perspective views of the intermediate segment shown in FIG. 26.
Figure 30:
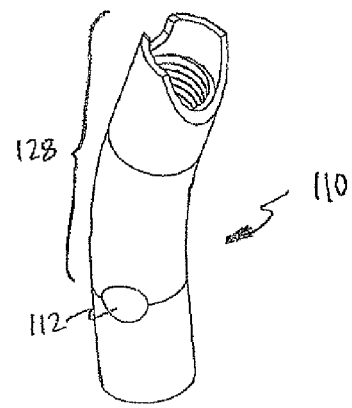
FIGS. 30 and 31 are perspective view of the proximal-most segment shown in FIG. 25.
Figure 29:
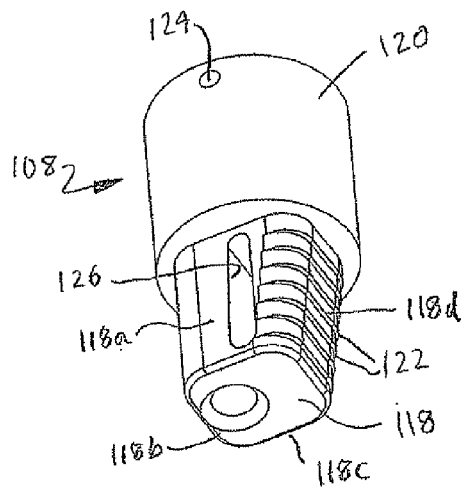
Figure 31:
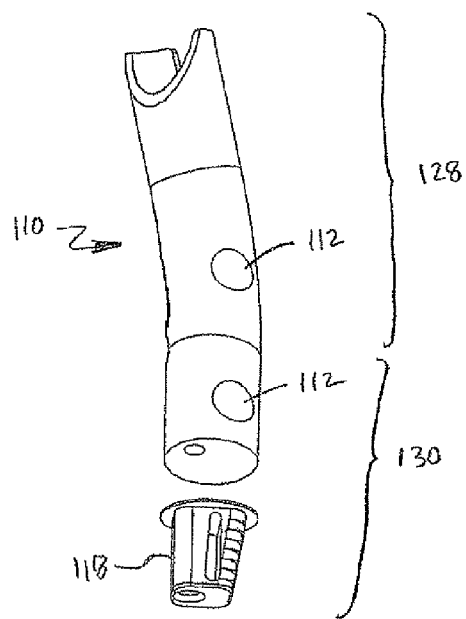
Figure 32:
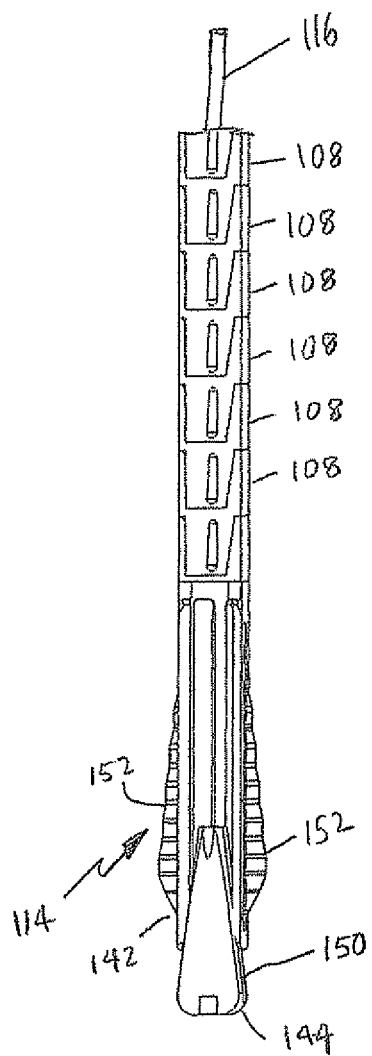
FIG. 32 is a cross-sectional view of the distal portion of the implantable fracture fixation device of FIG. 23, showing details as to the distal-most segment.
Figure 33:
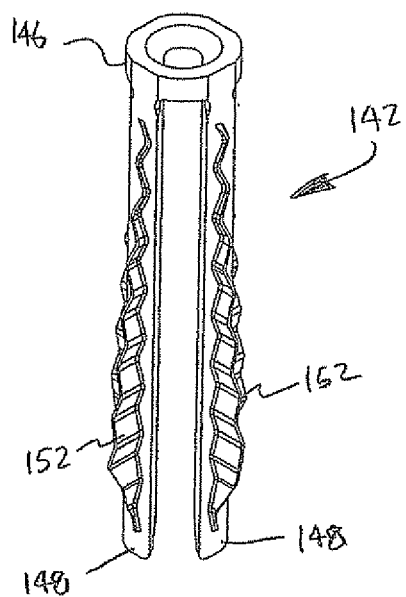
FIG. 33 is a perspective view of an expander forming a portion of the distal-most segment.

With reference to FIGS. 24-26, the implantable fixation structure 102 comprises a plurality of substantially identical, inter-fitting intermediate segments 108, (nine shown), a proximal end segment 110 having a plurality of holes or throughbores 112 adapted to receive fixation screws, and a radially-expandable distal end segment 114. A cable 116 is secured to the distal end segment that extends through the implantable structure beyond the proximal end segment 116 and through the cable tensioner 200 to apply a compressive force to the segments so as to result in a rigid implant. Each of the segments 108, 110 proximal to the distal end has an open interior to permit the tensioning cable 116 to pass therethrough and to allow the segments to slide along the cable 116 during insertion into the intramedullary canal.

The proximal end segment 110 and the intermediate segments 108 are pre-assembled, with the various segments hingedly secured to each other. In order to facilitate insertion of the fixation structure 102 into the head of a long bone, where the entry point for the implant is offset from the axis of the long bone, the various segments 108, 110 of the implantable structure are configured to be relatively moveable only axially and laterally in a single plane. To this end, and with reference to FIGS. 26, 28 and 29, the intermediate segments 108 have inter-fitting male and female portions, 118 and 120, respectively, that comprise three substantially planar faces (118*a*, 118*b* and 118*c* for the male portion, and 120*a*, 120*b* and 120*c* for the female portion). The faces 118*a*, 120*a* are generally parallel to faces 118*c*, 120*c*, respectively, while the faces 118*b* and 120*b* are generally perpendicular to the faces 118*a*, 118*b* and 120*a*, 120*b*, respectively. A fourth face 118*d*, 120*d* is obliquely oriented relative to the longitudinal axis of the segment. Adjacent surfaces are joined by an arcuate surface. The three planar surfaces ensure that the assembled structure is flexible substantially only in a plane substantially parallel to the parallel faces of the male and female portions of the segments.

Experience has shown that when members with smooth or regular tapered or conical surfaces nest, there is tendency for the tapered surfaces to lock together. This, of course, would be disadvantageous in the present structure, as it would result in a reduced flexibility of the implantable structure required for insertion into and removal from the intramedullary canal. Accordingly, the obliquely-oriented surfaces 118*d*, 120*d* of the male and female portions 118, 120 of the segments 108 are formed with a series of steps 122 having surfaces that are substantially parallel to the axis of the segment. This ensures that if tension is not applied to the cable 116, and the fixation structure 102 is not under compression, the mating portions of the segments freely slide apart.

The various segments 108, 110 of the structure are secured to each other in a manner that permits limited axial movement relative to the adjacent segments, and ensures the proper orientation of the faces of the male portion of a segment with the female portion of the adjacent segment. In the structure of the present embodiment, this is accomplished by providing the female portion 120 of the segment with a pin 124 (best seen in FIG. 28) lying in a plane perpendicular to that in which the assembled implant flexes. The pin 124 extends through the open interior of the female portion 120 of its associated segment and is captured in an axially-oriented, elongated slot 126 in the male portion 118 of the proximally adjacent segment. As seen in the drawings, the slot 126 is wider at the distal end than at the proximal end, providing for greater flexibility of the expanded implantable structure. Of course, the pin could be carried by the male portion 118 of the segment and ride in a slot in the female portion 120 to achieve the same result.

The proximal end segment 110 has an open interior for passage of the tensioning cable and comprises two sections: an arcuate section 128 and a mating section 130, the latter having a male portion 118 as described above for seating in the female portion 120 of the immediately distal intermediate segment. To allow for fixation of the proximal end of the implantable structure to the bone, the arcuate segment includes a plurality of throughbores 112 (three shown) oriented generally perpendicular to the axis of the implantable fixation structure 102 for the receipt of bone screws (not shown). The throughbores 112 are located so as to not intersect the open interior of the arcuate section, thus ensuring that the tensioning cable 116 is not contacted by the fixation screws.

The proximal end of the arcuate section 128 is configured to receive a two-part distal collet assembly 132 (FIGS. 35 and 39) for locking the tensioning cable 116 (as will be described in greater detail below) and to also seat the screw guide interface 104 in a predetermined orientation.

As described in connection with the prior embodiments, the distal portion of the implantable structure can be configured to be fixed to the bone by bone screws or by bone cement. However, in the present embodiment, the fixation of the implantable structure to the distal portion of the long bone is preferably accomplished by having the distal-most segment 140 be radially expandable so as to engage the surface of the intramedullary canal. To this end, and with reference to FIGS. 27, 32 and 33, the distal segment 140 comprises an expanding member 142 that receives a wedge member 144 on the interior thereof. The wedge member 144 is secured to the distal end of the tensioning cable so that as tension is placed on the cable 116, the wedge member 144 is moved proximally into the expanding member 142 to cause the expanding member 142 to radially expand into engagement with the surface of the intramedullary canal.

The illustrated expander 142 comprises an upper collar portion 146 from which depend in cantilever fashion a plurality of evenly radially-spaced legs 148 (four shown). In its undeformed state, the expander 142 has a radial dimension no greater than that of the other segments 108, 110 of the implantable fixation structure 102 in order to facilitate insertion into the intramedullary canal. The wedge member 144 is generally conical in shape, and has elongated grooves 150 in its surface for seating the legs 148 of the expander 142. Preferably, the grooves 150 have a cross-sectional shape that is complimentary to the inner surfaces of the legs 148.

In order to enhance the anchoring of the expander in the intramedullary canal, the outer surfaces of the legs may be formed with structures designed to more easily penetrate into the boney surface of the intramedullary canal. Such structures may take the form of points or a narrow edge or blade-like structure. In the illustrated embodiment, the outer surface of each leg is provided with a continuous raised spine 152. Preferably the spines 152 have a wavy or zig-zag configuration, which provides resistance to both axial and rotational movement of the embedded expander 142.

As noted above, in the present embodiment, the proximal end segment 110 includes three throughbores 112 for receiving bone screws to secure the proximal end of the implant 102 in position. To facilitate the placement of the screws, the proximal segment 110 is adapted to mount a screw guide interface 104. As best seen in FIGS. 34 and 35, the screw guide 104 comprises a pair of depending arms 154, 156, with a first arm 154 mounting a pair of guide tubes 158, 160 and a second arm 156 mounting a single guide tube 162. When the screw guide interface 104 is secured to the proximal end segment 110 of the implant 102, the guide tubes 158, 160, 162 are aligned with the throughbores 112. The upper ends of the arms 154, 156 are joined together, with a tubular-shaped segment 164 depending downwardly from the juncture of the arms 154, 156. The lower end of the tubular-segment 164 and the upper end of the proximal segment 110 are configured so that the screw guide interface 104 seats on the proximal segment 110 in proper orientation, with the screw guide tubes 156, 160, 162 aligned with their intended throughbores 112. Once properly seated, the screw guide interface 104 is secured to the implant by an insertion guide 166. The insertion guide 166 has an enlarged gripping surface 168 and a depending tubular section 170. The gripping surface 168 of the insertion guide 166 seats in a recessed portion of the screw guide interface 104, with the tubular section 170 of the insertion guide 166 extending through the tubular segment 164 of the screw guide interface 104 so as to be received in the proximal end of the proximal segment 110 of the implant 102. The distal end of the tubular section 170 of the insertion guide 166 is externally threaded, while the interior surface of the proximal end of the proximal segment 110 is internally threaded. Thus, the insertion guide 166 can be screwed into the proximal end segment 110 to secure the screw guide interface 104 in position on the implantable fixation device 102.

Figure 36:
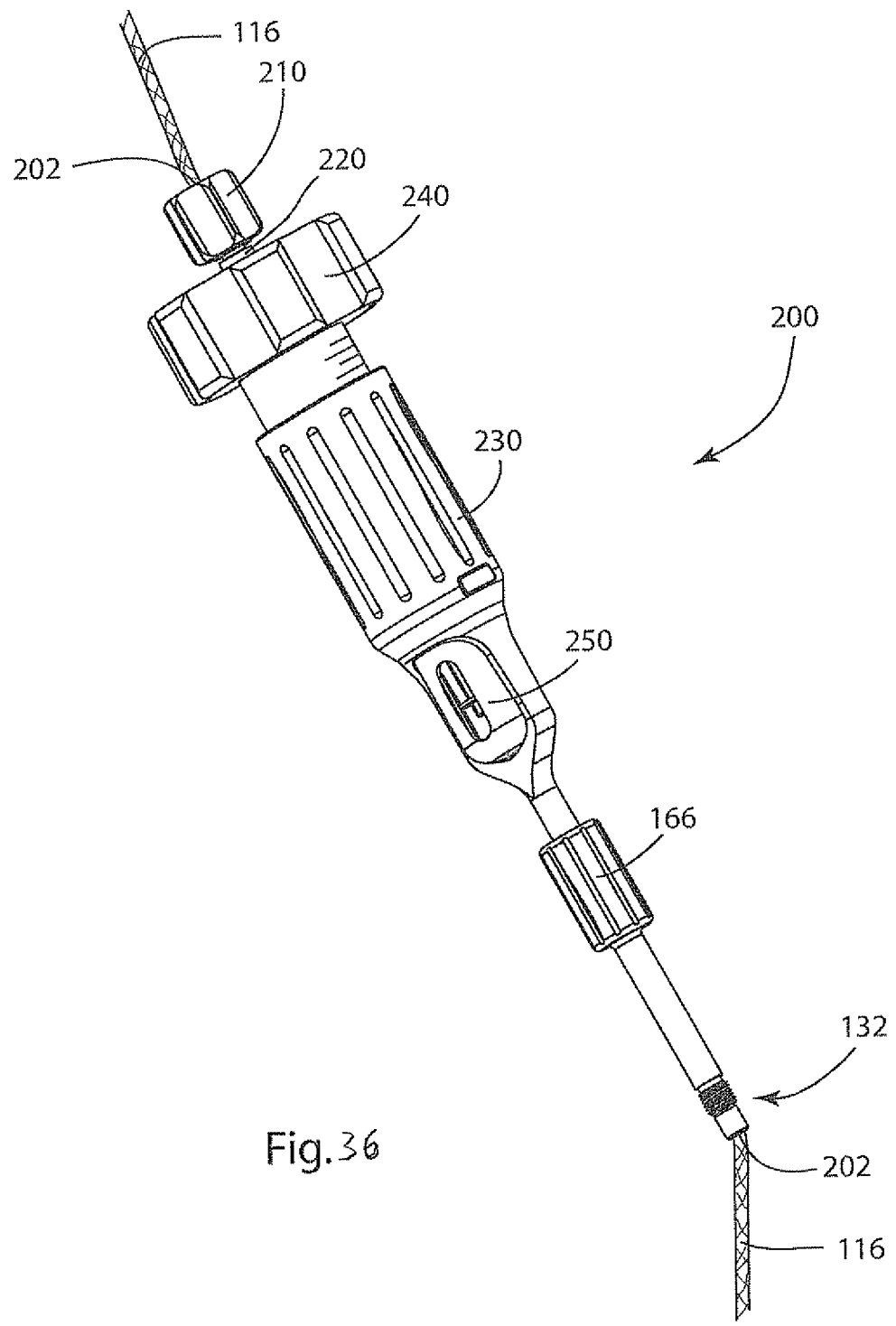
FIG. 36 is an enlarged perspective view of the cable tensioner.

A tensioner tool assembly may be utilized to regulate and/or lock tension on the cable in the fixation device. The tensioner tool assembly may comprise a cable, a locking feature, a tensioner, and a locking mechanism actuator. Referring to FIG. 36, a perspective view of one embodiment of a tensioner tool assembly 200 is shown. It is appreciated that the tensioner tool assembly 200 may be used to provide and regulate tension to a cable, cord, tether or other flexible member connected to a segmented intramedullary fracture fixation device as set forth above, or may be used to provide and regulate tension for other implants, devices or systems. When used with a segmented intramedullary fracture fixation device such as fixation device 102, the tensioner tool assembly 200 may be guided over the cable 116 (connected to and extending from the fixation device, not shown), and releasably attached to the proximal end of the device. A proximal collet screw, a tensioner and a distal collet assembly comprising a cable collet screw may be actuated in sequence to attain and lock down the tension on the cable in the fixation device at a preferred level. The tensioner tool assembly 200 may then be removed, and the cable extending outside of the fixation device 200 may be cut off, while the cable inside the fixation device remains at the preferred tension.

The embodiment of the tensioner tool assembly 200 comprises a proximal collet 210 which engages within a threaded shaft 220. Distal to the proximal collet is a threaded knob 240 which partially extends into a housing 230. The housing 230 is shaped to be dockable in the insertion guide 166, which can connect to the proximal end of the fixation device. A collet driver 250 is captured within the housing and is configured to be rotatable within the housing. Within the connection between the insertion guide and the fixation device is the distal collet assembly 132. A cable bore 202 extends longitudinally along a straight path within the entire length of the assembly 200.

When connecting the tensioner tool assembly 200 to the fixation device 102, first the insertion guide 166 may be guided over the cable 116 and attached to the fixation device 102, and then the remainder of the tensioner tool assembly 200 guided over the cable 116 and docked via the housing 230 within the insertion guide 166. Alternately, the tensioner tool assembly 200 may first be docked to the insertion guide 166, and the entire assembly then guided over the cable 116 and attached to the fixation device 102. Threads or other coupling features may provide an interface to dock the housing 230 to the insertion guide 166.

Figure 37:
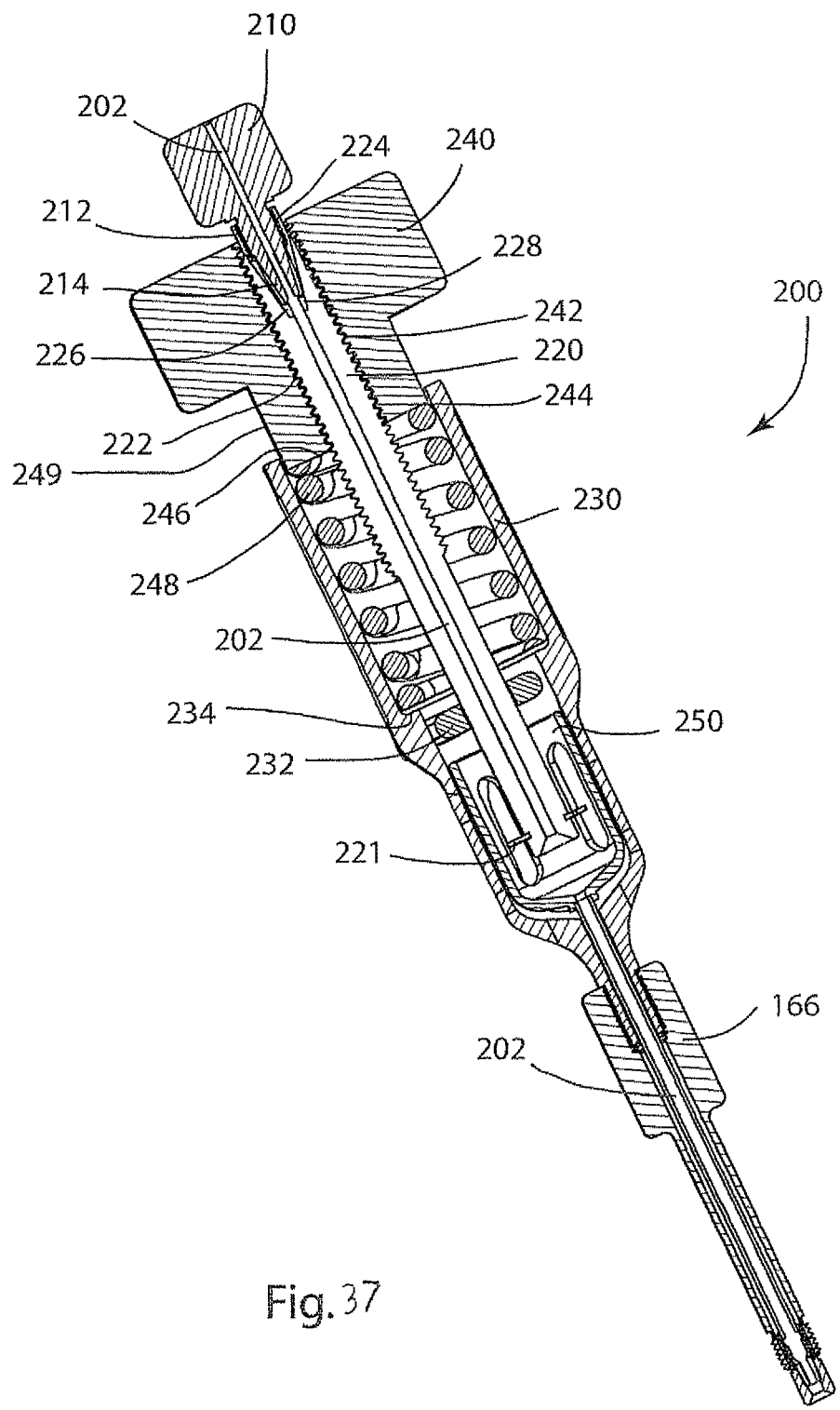
FIG. 37 is a cross-sectional view of the cable tensioner shown in FIG. 36.

Referring to FIG. 37, a longitudinal partial cross-sectional view of the tensioner tool assembly 200 is shown. For clarity in distinguishing the parts of the tensioner tool assembly, the cable is not shown. The cable bore 202 is seen extending the length of the assembly 200 along a straight path. The threaded knob 240 has an internally threaded lumen 242 through which the threaded shaft 220 extends, The threaded shaft 220 extends thru the lumen 242 from the proximal end of the threaded knob 240, and into the housing 230. A crossbar 232 through which the shaft 220 passes may provide an anti-rotation feature, preventing rotation of the shaft. A retaining feature 221 may retain the distal end of threaded shaft within the housing, preventing accidental withdrawal of the threaded shaft from the lumen 242. The threaded shaft 220 has external threads 222 which extend for a distance along its exterior. At the proximal end of the threaded shaft 220 is a short section of internal threads 224, and distal to the internal threads 224 is a chamber 226 with a tapered wall 228.

The proximal collet 210 fits into the proximal end of the threaded shaft 220. External threads 212 engage with the internal threads 224 on the threaded shaft to hold the collet 210. A plurality of flexible fingers 214 extend distally from the collet 210, into the chamber 226. As previously described, the tensioner tool assembly 200 is guided over the cable 116 (not shown), and the cable extends through the cable bore 202 and out the proximal end of the proximal collet 210. The proximal collet 210 is a locking feature which may be locked onto a location on the cable by screwing the proximal collet 210 into the threaded shaft 220. As the collet 210 is screwed in, the fingers 214 advance distally into the chamber 226. As the fingers 214 bias against the tapered wall 228, they are urged together, engaging and constricting the cable, until the cable is securely gripped. As the fingers 214 engage the cable, they may circumferentially surround the cable. In this position, the cable is locked and prevented from being pulled in either direction. However, the cable can again be freely moved by simply unscrewing collet 210 from within threaded shaft 220 so that fingers 214 are able to freely, outwardly flex and disengage from the cable. It is noted that in the locking process, the cable 116 remains oriented substantially along a straight path within the assembly 200 and is not bent, curved, crimped or severed.

Once the cable is locked, the tensioner may be actuated to regulate tension to the cable. The tensioner may comprise the housing 230, the threaded knob 240, the threaded shaft 220, the crossbar 232, and the retaining feature 221. The threaded knob 240 may be actuated by turning it to provide tension to the cable. As the knob 240 is turned, internal threads 244 engage with the external threads 222 on the threaded shaft 220, and the knob 240 moves distally while the threaded shaft 220 moves proximally as the rotational motion is translated into linear motion. Since the cable is connected to the fixation device at a first location at the distal end segment, and locked within the collet 210 within the shaft 220 at a second location, moving the shaft 220 proximally moves the collet 210 relative to the fixation device, putting tension on the cable between the first location at the fixation device and the second location at the collet.

As the knob 240 moves distally, a distal face 246 of the knob pushes on a spring 248 which surrounds the threaded shaft 220 in the housing 230. As the knob 240 is turned further, the spring 248 is compressed between the knob distal face 246 and a lip 234 formed in the wall of the housing 230. This compression may provide a measure of the amount of force applied to the knob. Indicator markings (shown in Figure A) may be present on the outside of a distal wall 249 of the threaded knob 240 to indicate the amount of force as the knob is turned. The knob 246 is actuated by turning either direction, increasing or decreasing the tension, until a preferred level of tension is reached.

Figure 38:
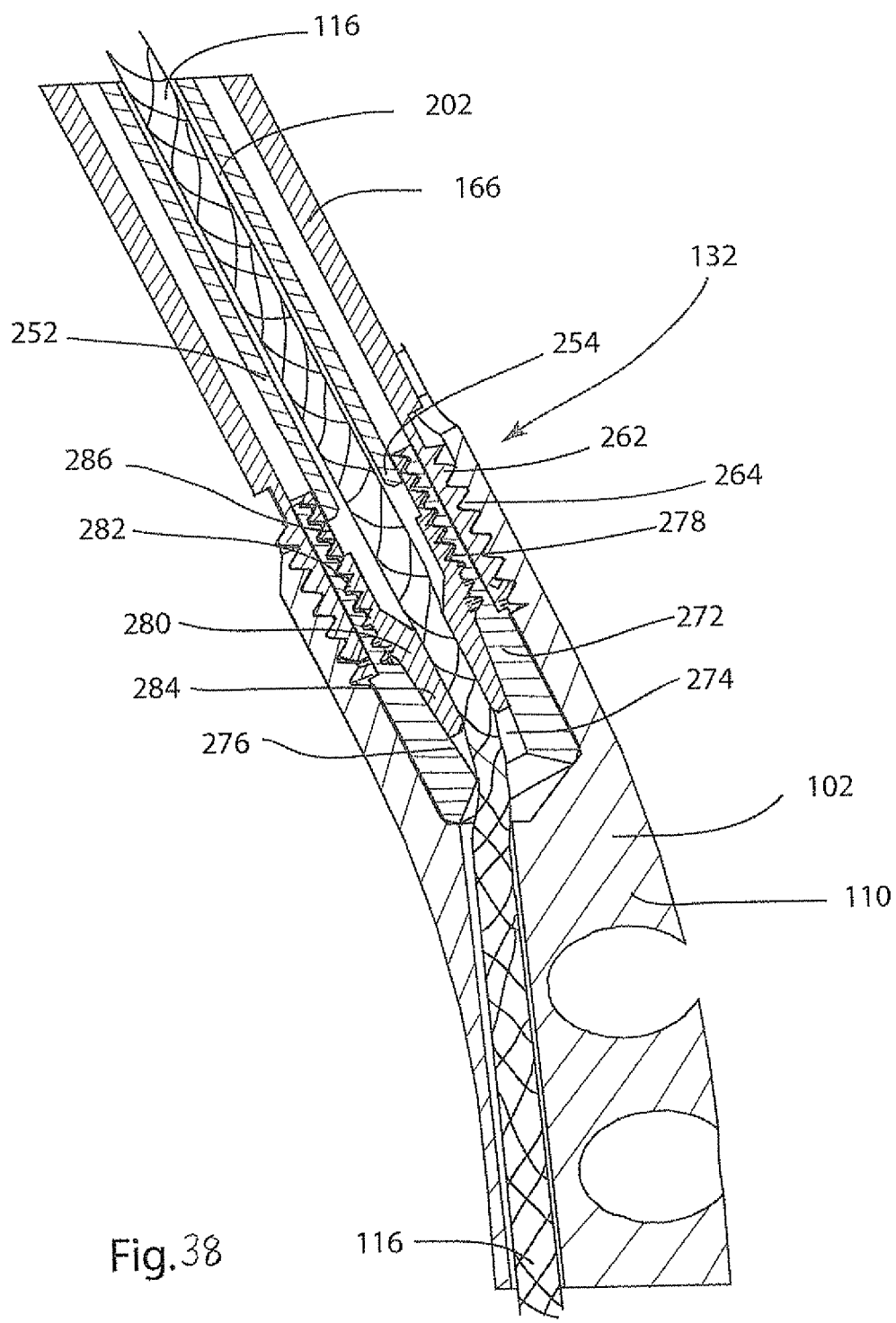
FIG. 38 is an enlarged cross-sectional view of the cooperating structure of the cable tensioner and the proximal-end segment of the fracture fixation device.

Referring to FIG. 38, a partial cross-sectional view of a cable 116 passing through the distal collet assembly 132, which is surrounded by a connection between a portion of the insertion guide 166 and a proximal end segment 110 of the fixation device 102, is shown. For clarity, the cable is not shown in cross-section, but a stylized outer surface of the cable is shown. External connection threads 262 on the insertion guide 166 engage with internal connection threads 264 on the fixation device 102 to hold the insertion guide 166 in a fixed position relative to the fixation device 102. A cable collet anchor 272 fits within the proximal end of the fixation device and extends for a short distance into the insertion guide 166. The cable collet anchor 272 may be integrally formed in the fixation device, or may be press-fit or otherwise connected. A chamber 274 having a tapered wall 276 is in a distal end of the cable collet anchor 272, and the proximal end of the cable collet anchor has internal collet threads 278.

A cable collet screw 280 fits within the cable collet anchor 272, held in place by external collet threads 282 which engage with the internal collet threads 278. At a proximal end of the cable collet screw, a shaped inner wall 286 surrounds the cable bore 202. A plurality of flexible fingers 284 extend distally, into the chamber 274. Together the cable collet screw 280 and the cable collet anchor 272 form a locking mechanism.

Extending distally through the insertion guide 166 is a driver shaft 252 of the collet driver 250. As seen in Figure B, the collet driver 250 is captured within the tensioner, but operates independently from the tensioner. A working end 254 of the driver shaft 252 is shaped to mate with the shaped inner wall 286 of the cable collet screw 280. The working end 254 may be shaped as a hexagon or any other shape configured to mate with the cable collet screw.

After the cable has been tensioned as set forth above, the collet driver 250 is actuated to actuate the locking mechanism which includes the cable collet screw 280 and anchor 272. To lock the position of the tensioned cable at a third location, which is relative to the fixation device 102, the cable collet screw 280 is tightened. To tighten the cable collet screw 280, the collet driver 250 is turned, turning the collet driver shaft 252. The working end 254 mates with the shaped inner wall 286 of the cable collet screw, and consequently the cable collet screw 280 is turned. As the collet screw 280 turns and advances within the anchor 272, the fingers 284 advance into the chamber 274. As the collet fingers 284 bias against the tapered wall 276, they are urged together, gripping the cable 116 and locking its position relative to the fixation device 102. In this position, cable 116 is prevented from being pulled in either direction. However, cable 116 can again be freely moved by simply unscrewing collet screw 280 from within the anchor 272 so that fingers 284 are able to freely, outwardly flex.

Once the cable 116 is locked in the cable collet screw 280, the tension on the cable relative to the fixation device 102 is fixed. The proximal collet 210 may be unscrewed, releasing its grip on the cable 116. The housing 230 may be undocked from the insertion guide 166, allowing removal of the tensioner tool 200 from the insertion guide 166. The insertion guide may then be unscrewed and removed from the fixation device 102, leaving the cable 116 locked in the cable collet screw 280. Alternately, the housing 230 may remain docked within the insertion guide 166, and the insertion guide 166 may be uncoupled from the fixation device 102, bringing the docked tensioner tool 200 with it. After both the insertion guide and tensioner tool are removed, the cable 116 extending proximally from the distal collet screw 280 may be cut to a preferred length.

Thus, an improved intramedullary structure has been provided as described above. While the structure has been described in terms of certain specific embodiments, there is no intention to limit the invention to the same. Instead, the invention is defined by the scope of the following claims.

What is claimed is:

1. A method for tensioning a surgical cable in an implant, the method comprising:
providing an implant connected to a first location on a cable;
locking a locking feature onto a second location on the cable, wherein the locking feature comprises a plurality of fingers and a tapered wall, the plurality of fingers being configured to circumferentially engage the cable to lock onto the cable;
actuating a tensioner to regulate the tension on the cable between the first location and the second location; and
locking a locking mechanism on the implant onto a third location on the cable by actuating a locking mechanism actuator to lock the locking mechanism on the implant onto the third location on the cable after regulating the tension on the cable.

2. The method of claim 1, wherein the implant is a segmented intramedullary fracture fixation device.

3. The method of claim 1, wherein the third location is between the first location and the second location.

4. The method of claim 1, further comprising cutting the cable after locking the locking mechanism.

5. A method for tensioning a surgical cable in an implant, the method comprising:

provapping a cable connected to an implant at a first location on the cable;

locking a locking feature onto a second location on the cable, wherein the locking feature comprises a plurality of fingers and a tapered wall, the plurality of fingers being configured to circumferentially engage the cable to lock onto the cable;

actuating a tensioner to regulate the tension on the cable between the first location and the second location;

locking a locking mechanism on the implant onto a third location on the cable;

actuating a locking mechanism actuator to lock the locking mechanism on the implant onto the third location on the cable after regulating the tension on the cable, wherein the implant is locked in a tensioned state; and releasing the locking feature at the second location on the cable.

6. The method of claim 5, wherein the implant is a segmented intramedullary fracture fixation device.

7. The method of claim 5, wherein the third location is between the first location and the second location.

8. The method of claim 5, further comprising cutting the cable after locking the locking mechanism.

* * * * *